(12) United States Patent
Kai

(10) Patent No.: US 12,103,992 B2
(45) Date of Patent: Oct. 1, 2024

(54) POLYMER MATERIAL AND INTRAOCULAR LENS

(71) Applicant: Shanghai Fulo Medical Instrument Co., Ltd., Shanghai (CN)

(72) Inventor: Mototora Kai, Shanghai (CN)

(73) Assignee: Shanghai Fulo Medical Instrument Co., Ltd., Shanghai (CN)

( * ) Notice: Subject to any disclaimer, the term of this patent is extended or adjusted under 35 U.S.C. 154(b) by 954 days.

(21) Appl. No.: 15/734,039

(22) PCT Filed: May 21, 2019

(86) PCT No.: PCT/CN2019/087749
§ 371 (c)(1),
(2) Date: Jun. 8, 2021

(87) PCT Pub. No.: WO2019/228224
PCT Pub. Date: Dec. 5, 2019

(65) Prior Publication Data
US 2021/0292447 A1 Sep. 23, 2021

(30) Foreign Application Priority Data
Jun. 1, 2018 (JP) .................................. 2018-106165

(51) Int. Cl.
C08F 20/44 (2006.01)
A61L 27/14 (2006.01)
(Continued)

(52) U.S. Cl.
CPC .............. *C08F 20/30* (2013.01); *A61L 27/16* (2013.01); *A61L 27/50* (2013.01); *C08F 20/14* (2013.01);
(Continued)

(58) Field of Classification Search
CPC .. A61L 27/14; A61L 27/50; C08F 2/44; C08F 20/14; C08F 20/26; C08F 20/44
See application file for complete search history.

(56) References Cited

U.S. PATENT DOCUMENTS 5,603,774 A 2/1997 LeBoeuf
5,693,095 A 12/1997 Freeman et al.
(Continued)

FOREIGN PATENT DOCUMENTS

CN 1155845 A 7/1997
CN 1290352 A 4/2001
(Continued)

OTHER PUBLICATIONS

Extended European Search Report, EP application No. 19811260.9, Feb. 14, 2022 (8 pages).
(Continued)

*Primary Examiner* — Caixia Lu
(74) *Attorney, Agent, or Firm* — HSML P.C.

(57) ABSTRACT

A polymer material is provided that can be used to produce an intraocular lens having a high refractive index and low adhesion on a lens surface and suppressing the occurrence of glistening and sub-surface nano glistening. Further, an intraocular lens with the properties mentioned above is provided. The polymer material can preferably be used to produce an intraocular lens. The polymer material is formed by polymerizing a liquid monomer mixture containing 11 to 30% by mass of a macromonomer (A) represented by the following formula (I) and at least a (meth)acrylate monomer (B) with an aryl group.

(Continued)

$$\text{Z} \mathord{-\!\!\!\!-\!\!(\!}\text{OH}_2\text{CH}_2\text{C}\!\!\mathord{)_{\overline{d}}}\!\!\text{O} \mathord{-\!\!\!\!-\!\!(\!}\text{H}_2\text{C}\!\!\mathord{)_{\overline{n}}}\!\!\overset{\overset{\displaystyle \text{O} \mathord{-\!\!\!\!-\!\!(\!}\text{CH}_2\text{CH}_2\text{O}\!\mathord{)_{\overline{a}}}\!\!\text{Z}}{\overset{\displaystyle |}{\underset{\overline{n}}{\overset{\displaystyle \text{CH}_2}{|}}}}}{\underset{\underset{\displaystyle \text{O} \mathord{-\!\!\!\!-\!\!(\!}\text{CH}_2\text{CH}_2\text{O}\!\mathord{)_{\overline{c}}}\!\!\text{Z}}{\underset{\displaystyle |}{\overset{\overline{n}}{\underset{\displaystyle \text{CH}_2}{|}}}}}{\text{C}}} \mathord{-\!\!\!\!-\!\!(\!}\text{CH}_2\!\mathord{)_{\overline{n}}}\!\!\text{O} \mathord{-\!\!\!\!-\!\!(\!}\text{CH}_2\text{CH}_2\text{O}\!\mathord{)_{\overline{b}}}\!\!\text{Z} \qquad (\text{I})$$

[In the formula, four n respectively and individually representing 1 or 2, a, b, c, and d being respectively and individually integers of 4 or more, and four Z being respectively and individually substituent groups containing a (meth)acryloyl group.]

14 Claims, 3 Drawing Sheets

(51) Int. Cl.
  *A61L 27/16* (2006.01)
  *A61L 27/50* (2006.01)
  *C08F 20/14* (2006.01)
  *C08F 20/26* (2006.01)
  *C08F 20/30* (2006.01)
  *A61F 2/16* (2006.01)
(52) U.S. Cl.
  CPC . *A61F 2002/16965* (2015.04); *A61L 2430/16* (2013.01)

(56) References Cited

U.S. PATENT DOCUMENTS

| | | | |
|---|---|---|---|
| 6,353,069 | B1 | 3/2002 | Freeman et al. |
| 8,048,154 | B2 | 11/2011 | Schlueter |

FOREIGN PATENT DOCUMENTS

| | | |
|---|---|---|
| CN | 104136050 A | 11/2014 |
| EP | 0485197 A1 | 5/1992 |
| EP | 2673666 A1 | 12/2013 |
| JP | 4-292609 A | 10/1992 |
| JP | 8-224295 A | 9/1996 |
| JP | 2014-125557 A | 7/2014 |
| JP | 2015-025063 A | 2/2015 |
| JP | 2015-512665 A | 4/2015 |
| WO | 96/40303 A1 | 12/1996 |
| WO | 99/53347 A1 | 10/1999 |
| WO | 2013/122584 A1 | 8/2013 |

OTHER PUBLICATIONS

Examination Report, European Patent Application No. 19811260.9, Mar. 10, 2023 (4 pages).
Office Action issued in Chinese Patent Application No. 201980036577. 9, Nov. 9, 2022, with English translation (14 pages).
Office Action issued in European Patent Application No. 19811260. 9, Sep. 29, 2022 (6 pages).
International Search Report and Written Opinion, International Patent Application No. PCT/CN2019/087749, Jul. 29, 2019, with English translation (21 pages).
Examination Report, European Patent Application No. 19811260.9, Jun. 27, 2022 (6 pages).

POLYMER MATERIAL AND INTRAOCULAR LENS

TECHNICAL FIELD

The invention relates to a polymer material and an intraocular lens. More specifically, the invention relates to a polymer material capable of being made into an intraocular lens that has a high refractive index, low adhesion on a lens surface, and suppresses the occurrence of glistening and sub-surface nano glistening, and an intraocular lens having the properties mentioned above.

BACKGROUND TECHNIQUE

The development of flexible and foldable intraocular lens materials for use as intraocular lenses has attracted much attention as small-incision cataract surgery has advanced.

To reduce the thickness of such an intraocular lens, it is necessary to make such an intraocular lens material have a high refractive index. In addition, the intraocular lens can be rolled or folded such that it can be inserted into the eye via a small incision. For this reason, the intraocular lens material certainly needs to be flexible, and also needs to have low adhesion, so as to avoid surfaces of optical parts from fitting to reduce the operability.

Furthermore, after the intraocular lens material is inserted into the eye, it is important that the intraocular lens material does not undergo the phenomenon that hydration and aggregation make moisture appear in a dot shape and reduces its transparency significantly, that is, so-called glistening and sub-surface nano glistening.

Known intraocular lens materials include a flexible acrylic material with a high refractive index (for example, referring to Patent Document 1). Patent Document 1 discloses an acrylic material with a high refractive index, suitable for the intraocular lens material. The acrylic material can be folded and inserted into the eye through the small incision.

Here, to improve the flexibility of the intraocular lens material, it is effective to lower its glass transition temperature. Generally, by selecting two or more from monomers that constitute respective homopolymers having different glass transition temperatures and changing their blending ratios to carry out polymerization, a polymer with an adjusted glass transition temperature is obtained.

For example, compared with the homopolymer of methacrylate monomers, the homopolymer of acrylate monomers has a relatively low glass transition temperature. Therefore, in intraocular lens materials, a relatively large amount of acrylate monomers is blended.

However, as the amount of the blended acrylate monomers increases, the surface adhesion of intraocular lens materials enhances, and the surfaces of optical parts become easy to fit with each other during rolling or folding. Therefore, the operability of the intraocular lens decreases, or the time taken for the intraocular lens to return to its original shape becomes longer, which is not preferable.

In addition, attempts have been made to reduce the adhesion of the foldable acrylic materials (for example, referring to Patent Document 2). In Patent Document 2, fluorine-based monomers are used as one of components so as to reduce the adhesion of the acrylic materials. In addition, there have been proposed a method of reducing the adhesion of the optical part surfaces of the intraocular lens materials by plasma treatment on the surfaces (for example, referring to Patent Document 3).

However, in Patent Document 2, by blending fluorine-based monomers with a low refractive index, the refractive index of the obtained acrylic materials (intraocular lens materials) is reduced. In addition, the method based on surface modification as proposed in Patent Document 3 requires large-scale equipment and therefore results in complicated process, so it is not preferable for mass production of intraocular lenses (intraocular lens materials). In addition, even if the adhesion is improved, the problem that the intraocular lens material tends to cause glistening and sub-surface nano glistening after being inserted into the eye has not been solved yet.

Glistening and sub-surface nano glistening are caused by the presence of trace amounts of water contained in the acrylic material. The intraocular lens exists in aqueous humor in the eye, absorbs water from the aqueous humor and is stabilized in the state of saturated water absorption. The temperature of the aqueous humor is easily affected by inflammation, body temperature, and even changes in the external environment. When the temperature in the eye decreases, the water absorption rate of the intraocular lens decreases, and the water in the intraocular lens that has been absorbed becomes supersaturated. It is considered that because the supersaturated water has no escape space, an uneven part of the three-dimensional network structure of the intraocular lens material undergoes phase separation, thereby causing glistening and sub-surface nano glistening.

An intraocular lens using a bifunctional polyethylene glycol group-containing component (monomer and/or cross-linking agent) for the purpose of improving glistening and sub-surface nano glistening is disclosed (for example, referring to Patent Document 4). Here, to improve glistening and sub-surface nano glistening, more components containing polyethylene glycol groups are required, but since polyethylene glycol groups are a factor that causes the refractive index of the intraocular lens to decrease, it is preferred to use a small usage amount of the polyethylene glycol groups.

However, in the bifunctional polyethylene glycol group-containing component disclosed in Patent Document 4, if a large amount of the polyethylene glycol groups is not used, glistening and sub-surface nano glistening cannot be improved.

In addition, an intraocular lens using a multi-functional polyethylene glycol group-containing component is disclosed (for example, referring to Patent Document 5).

However, by the usage amount of the multi-functional polyethylene glycol group-containing component disclosed in Patent Document 5, glistening and sub-surface nano glistening cannot be fully improved.

In addition, if the usage amount of the multi-functional polyethylene glycol group-containing component is too small, the glass transition temperature of the obtained intraocular lens material tends to increase, which means the flexibility tends to decrease. However, in Patent Document 5, the relationship between the usage amount of the multi-functional polyethylene glycol group-containing component and the flexibility of the intraocular lens is not discussed at all.

DOCUMENTATION OF THE PRIOR ART

Patent Documents

Document 1: JP H4-292609 A
Document 2: JP H8-224295 A
Document 3: Specification of U.S. Pat. No. 5,603,774
Document 4: Specification of U.S. Pat. No. 6,353,069
Document 5: JP 2015-512665 A

BRIEF SUMMARY OF THE INVENTION

Technical Problems to be Solved by the Invention

The object of the invention is to provide a polymer material capable of being made into an intraocular lens that has a high refractive index and low adhesion on a lens surface, and suppresses the occurrence of glistening and sub-surface nano glistening.

In addition, the another object of the invention is to provide a polymer material with quite readily adjustable flexibility (glass transition temperature).

Still another object of the invention is to provide an intraocular lens with the properties mentioned above.

Technical solutions for solving the technical problems mentioned above These objects are achieved by aspects (1)-(13) below of the invention.

(1) A polymer material is formed by polymerizing a liquid monomer mixture containing 11 to 30% by mass of a macromonomer (A) represented by the following formula (I) and at least a (meth)acrylate monomer (B) with an aryl group.

[Chemical Formula 1]

$$Z\text{-}(OH_2CH_2C)_{\overline{d}}\text{-}O\text{-}(H_2C)_{\overline{n}}\text{-}\underset{\underset{(CH_2)_{\overline{n}}}{|}}{\overset{\overset{O\text{-}(CH_2CH_2O)_{\overline{a}}\text{-}Z}{|}}{\underset{|}{C}}}\text{-}(CH_2)_{\overline{n}}\text{-}O\text{-}(CH_2CH_2O)_{\overline{b}}\text{-}Z \quad (I)$$

[In the formula, four n respectively and individually representing 1 or 2, a, b, c, and d being respectively and individually integers of 4 or more, and four Z being respectively and individually substituent groups containing a (meth)acryloyl group.]

(2) For the polymer material according to (1) mentioned above, in the formula (I), the a, b, c, and d are respectively and independently integers from 4 to 14, and a total of the a, b, c, and d is an integer from 16 to 56.

(3) For the polymer material according to (1) or (2) mentioned above, in the formula (I), each of the Z is represented by a formula (Z1), (Z2), or (Z3) below.

[Chemical Formula 2]

$$H_2C=\underset{\underset{R_1}{|}}{C}-\underset{\underset{O}{\|}}{C}- \quad (Z1)$$

$$H_2C=\underset{\underset{R_1}{|}}{C}-\underset{\underset{O}{\|}}{C}-O-CH_2CH_2-\underset{\underset{H}{|}}{N}-\underset{\underset{O}{\|}}{C}- \quad (Z2)$$

$$H_2C=\underset{\underset{R_1}{|}}{C}-\underset{\underset{O}{\|}}{C}-O-CH_2CH_2-O-CH_2CH_2-\underset{\underset{H}{|}}{N}-\underset{\underset{O}{\|}}{C}- \quad (Z3)$$

[In each formula, $R_1$ is a hydrogen atom or a methyl group.]

(4) For the polymer material according to any one of (1)-(3) mentioned above, in the formula (I), the four Z are identical.

(5) For the polymer material according to (4) mentioned above, in the formula (I), each of the four Z is an acryloyl group.

(6) For the polymer material according to any one of (1)-(5) mentioned above, the (meth)acrylate monomer (B) is represented by the following formula (II).

[Chemical Formula 3]

$$H_2C=\underset{\underset{R_2}{|}}{C}-\underset{\underset{O}{\|}}{C}-O-(CH_2)_{\overline{m}}Y-\phantom{xx}D \quad (II)$$

[In the formula, $R_2$ is a hydrogen atom or a methyl group, m is an integer from 1 to 6, Y is a direct bond or an oxygen atom, and D is a hydrogen atom, $-C_6H_5$, $-CH_2C_6H_5$, or $-OC_6H_5$.]

(7) For the polymer material according to any one of (1)-(6) mentioned above, the liquid monomer mixture contains 70-89% by mass of the (meth)acrylate monomer (B).

(8) For the polymer material according to any one of (1)-(7) mentioned above, the liquid monomer mixture further contains a polymerizable monomer with ultraviolet absorptivity.

(9) For the polymer material according to any one of (1)-(8) mentioned above, the liquid monomer mixture further contains a polymerizable monomer with a dyeing property.

(10) For the polymer material according to any one of (1)-(9) mentioned above, the liquid monomer mixture further contains at least one auxiliary monomer selected from the group consisting of a (meth)acrylate monomer with no aryl group and a cross-linking monomer.

(11) For the polymer material according to any one of (1)-(10) mentioned above, the polymer material is an intraocular lens material.

(12) An intraocular lens includes a processed article of the intraocular lens material according to (11) mentioned above.

(13) An intraocular lens includes the polymer material according to any one of (1)-(10) mentioned above.

Effects of the Invention

According to the invention, it is possible to produce the intraocular lens that has a high refractive index and low adhesion on a lens surface and suppresses the occurrence of glistening and sub-surface nano glistening. In addition, according to the invention, merely by changing the usage amount (blending amount) of the macromonomer (A), the glass transition temperature (i.e., flexibility) of the intraocular lens (polymer material) can be easily adjusted.

DETAILED DESCRIPTION OF THE INVENTION

Figure 1:
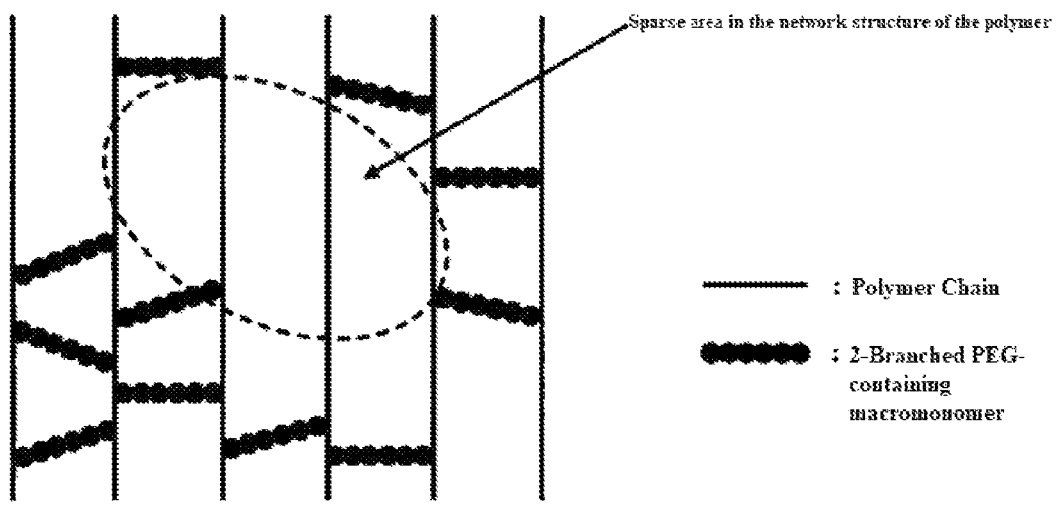
FIG. 1 is a simplified model diagram showing a polymer network formed when a macromonomer having a polyethylene glycol group in two branches is used.

The polymer material and the intraocular lens of the invention are described in detail below. Besides, in the text which follows, the polymer material of the invention used as an intraocular lens material is described as a representative.

<Liquid Monomer Mixture>

The liquid monomer mixture is preferably a monomer composite which can be used to make an intraocular lens (intraocular lens material). The liquid monomer mixture contains a macromonomer (A) and at least a (meth)acrylate monomer (B) with an aryl group.

<<Macromonomer (A)>>

The macromonomer (A) is (meth)acrylate monomer that has a polyethylene glycol group in four branches. The macromonomer (A), as represented by the formula [I] below, has four polyethylene glycol groups and four (meth)acryloyl groups in one molecule.

[Chemical Formula 4]

$$Z-(OH_2CH_2C)_d-O-(H_2C)_n-\underset{\underset{\underset{O-(CH_2CH_2O)_c-Z}{|}}{\underset{(CH_2)_n}{|}}}{\overset{\overset{\overset{O-(CH_2CH_2O)_a-Z}{|}}{\underset{(CH_2)_n}{|}}}{C}}-(CH_2)_n-O-(CH_2CH_2O)_b-Z \quad (I)$$

[In the formula, four n respectively and individually represent 1 or 2; a, b, c, and d are respectively and individually integers of 4 or more; and four Z are respectively and individually substituent groups containing a (meth)acryloyl group.]

Here, "(meth)acryloyl group" herein refers to a methacryloyl group or an acryloyl group.

The macromonomer (A) is used as one of the components, so the adhesion of the intraocular lens material can be suppressed while flexibility is imparted to the intraocular lens material, allowing suppression of the occurrence of glistening and sub-surface nano glistening.

Previously, by combining two or more (meth)acrylate monomers constituting respective homopolymers having different glass transition temperatures changing their blending ratios to carry out polymerization, a copolymer with an adjusted glass transition temperature is obtained. On the contrary, in the invention, merely by appropriately changing the usage amount of the macromonomer (A), the glass transition temperature (flexibility) of the intraocular lens material can be adjusted.

The molecular weight of the macromonomer (A) is preferably about 1,000 to 3,000, and more preferably about 1,400 to 2,800. By using the macromonomer (A) with the above molecular weight, the obtained intraocular lens material can be provided with flexibility and functions of suppressing glistening and sub-surface nano glistening, and a homogeneous liquid monomer mixture can also be obtained.

The molecular weight of the macromonomer (A) can be calculated on the basis of the saponification value of the macromonomer (A), and can also be expressed as a polystyrene-equivalent number-average molecular weight by determination based on gel permeation chromatography (GPC).

Such a macromonomer (A) can be, for example, synthesized by the following procedure.

[1] First, a 4-branched polyethylene glycol as a starting material is synthesized.

The 4-branched polyethylene glycol can be synthesized, for example, by the following two schemes.

The first scheme refers to a method of synthesizing the 4-branched polyethylene glycol in which the number of polyethylene glycol group repetitions is distributional. According to this method, ethylene oxide is subjected to addition polymerization with pentaerythritol in the presence of an alkaline catalyst.

[Chemical Formula 5]

$$\underset{HO}{\overset{HO}{\diagdown}}\hspace{-2pt}\underset{\diagup}{\overset{\diagup}{\times}}\hspace{-2pt}\underset{OH}{\overset{OH}{\diagup}} + \triangle\!\!\!\!\!O \longrightarrow$$

4-Branched polyethylene glycol

The second scheme refers to a method of synthesizing the 4-branched polyethylene glycol in which the number of polyethylene glycol group repetitions is not distributional.

Usually, when the number of repetitions (average value) of polyethylene glycol is 4 or above, a plurality of types having different numbers of repetitions is mixed.

Therefore, first polyethylene glycol is purified by a column to obtain polyethylene glycol (Compound 1) with a uniform (single) number of repetitions.

Second, after Compound 2 with polyethylene glycol protected by trityl chloride at one end is obtained, pentaerythrityl tetrabromide is reacted with the other end to obtain 4-branched polyethylene glycol with protected ends (Compound 3).

Finally, 4-branched polyethylene glycol is obtained through deprotection.

In addition, "TRT" in the following scheme refers to a trityl group.

[Chemical Formula 6]

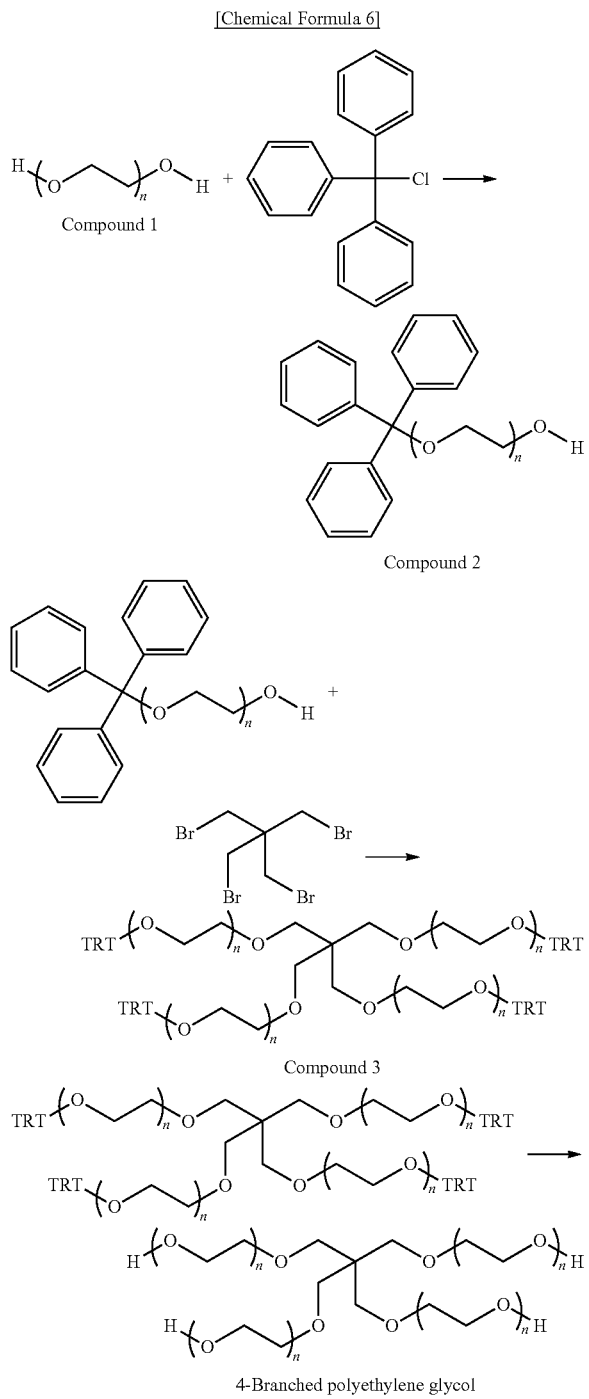

[Chemical Formula 7]

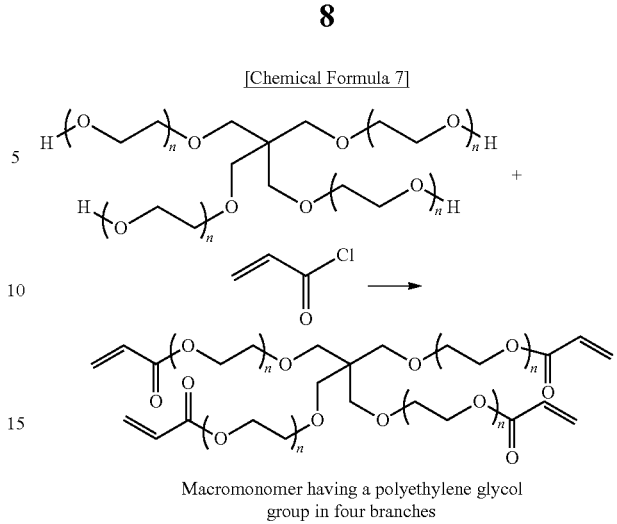

Macromonomer having a polyethylene glycol group in four branches

In addition, under the condition of introducing a substituent group containing a residual group of a (meth)acryloyl group and a carbamate group, for example, 2-isocyanate ethyl (meth)acrylate, 2-(2-isocyanate ethoxy) ethyl (meth)acrylate, or the like are reacted with 4-branched polyethylene glycol, in the presence of a tin-based urethanization catalyst or a non-tin-based urethanization catalyst.

In the formula (I), each Z may be a substituent group containing a (meth)acryloyl group, and may be the (meth)acryloyl group itself, or may be a group containing a (meth)acryloyl group and a bonding group (for example, amide group (residual group of the carbamate group), a keto group, etc.) which is bonded to an end of polyethylene glycol.

In the latter case, a linking group (for example, an alkylene oxide group, an alkylene group, etc.) may exist between the (meth)acryloyl group and the bonding group.

Among them, each Z is preferably a substituent group represented by a formula (Z1), (Z2), or (Z3) below, and is more preferably an acryloyl group.

[Chemical Formula 8]

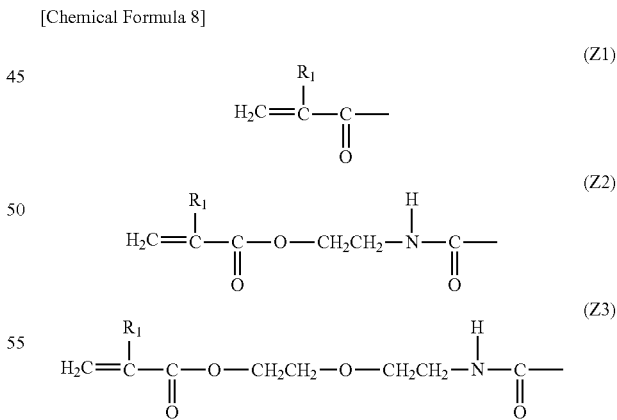

[In each formula, $R_1$ is a hydrogen atom or a methyl group.]

[2] Next, by introducing the substituent group to the ends of the obtained 4-branched polyethylene glycol, the macromonomer (A) is obtained.

Under the condition that a (meth)acrylate group is introduced as the substituent, methacryloyl chloride or acryloyl chloride is reacted with 4-branched polyethylene glycol in the presence of a dehydrohalogenation catalyst.

These substituent groups can be easily and reliably introduced to the ends of the 4-branched polyethylene glycol. In particular, use of the 4-branched polyethylene glycol in which the acryloyl group as the substituent group is introduced to each end can lower the glass transition temperature of the intraocular lens material.

In addition, in the formula (I), the four Z may be different from each other, but are preferably identical. By making the four Z be identical substituent groups (particularly acryloyl groups), the synthesis of the macromonomer (A) can be easily carried out, and the variation between batches can be reduced.

Specifically, the macromonomer (A) can be represented by a structural formula A1, A2, A3, or A4 below.

[Chemical Formula 9]

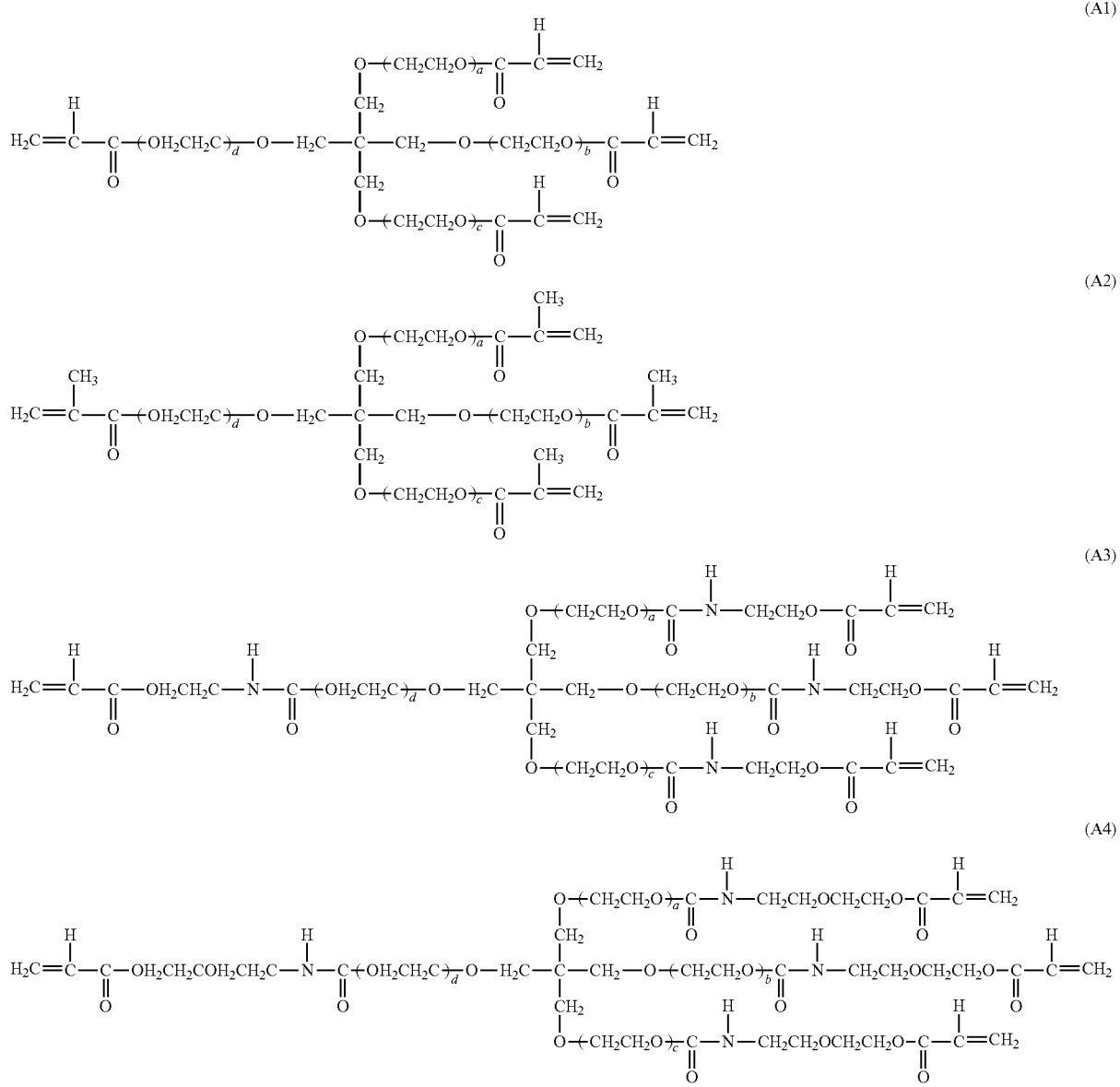

Herein, "polyethylene glycol group" and "polyethylene glycol" refer to structures in which the number of repetitions (a, b, c, and d each in formula (1)) of ethylene oxide is 4 or more.

In addition, in the formula (I), the values of a, b, c, and d may each be distributional (which means the values may be non-uniform), or may each be not distributional (which means that the values may be uniform). When the values of a, b, c, and d are distributional respectively, the average values thereof are integers of 4 or more. In addition, that the values of a, b, c, and d are not distributional refers to that, for example, when the values of a, b, c, and d are 6 respectively, other values (for example, 5, 7, etc.) are not included.

The values of a, b, c, and d are each preferably an integer from 4 to 14, and more preferably an integer from 6 to 12.

In addition, the total of a, b, c, and d is preferably an integer from 16 to 56, and more preferably an integer from 24 to 48.

Setting a, b, c, and d each to values of these lower limits or more can provide the intraocular lens material with higher flexibility and better suppress occurrence of glistening and sub-surface nano glistening. On the other hand, setting a, b, c, and d each to values of these upper limits or less can improve compatibility with other copolymerization components (other monomers), so as to obtain a more homogeneous liquid monomer mixture.

In particular, from the viewpoint of making the structure of a polymer obtained through polymerization of the monomers contained in the liquid monomer mixture uniform, it is preferable to make the lengths of the four branched chains as uniform as possible, and accordingly, a, b, c, and d are preferably approximate values to each other.

Herein, "average value" applies to the case that the number of repetitions of the polyethylene glycol group in the macromonomer (A) is distributional. Specifically, "average value" refers to a value obtained by rounding down the first digit after the decimal point of the number of repetitions that is calculated using the peak integrated intensity ratio of an ethylene oxide unit during $^1$H-NMR analysis of the macromonomer (A).

In addition, "macromonomer" herein refers to a monomer with a molecular weight of 900 or more.

The inventor made various investigations for the purposes of constraining the adhesion of the intraocular lens material, imparting flexibility to the intraocular lens material, and suppressing the occurrence of glistening and sub-surface nano glistening. Based on the results, the inventor discovered that although the detailed mechanism is not clear yet, the above purposes can be achieved by using the macromonomer (A) ranging from 11% to 30% by mass. Besides, it was also discovered that, the flexibility (glass transition temperature) of the intraocular lens (polymer material) can be adjusted merely by appropriately changing the usage amount of the macromonomer (A). Then, the inventor has come to complete the invention based on the above findings.

Here, in a macromonomer having a polyethylene glycol group and a (meth)acrylate group in one molecule, there are compounds having various structures represented by the following formulas. In addition, in the formula, the polyethylene glycol group is referred to as "PEG", and in the text which follows, the macromonomer having a polyethylene glycol group may be referred to as "PEG-containing macromonomer".

As representative structures of PEG-containing macromonomer, there are a 2-branched type, a 3-branched type, a 4-branched type, and an 8-branched type.

taining macromonomer") has a non-uniform structure due to random cross-linking, and the network structure of the polymer includes dense areas and sparse areas (refer to FIG. 1). Since water is phase-separated in the sparse areas of the network structure of the polymer, glistening and sub-surface nano glistening tend to occur. The tendency also exists in the 3-branched and 8-branched PEG-containing macromonomers.

Figure 2:
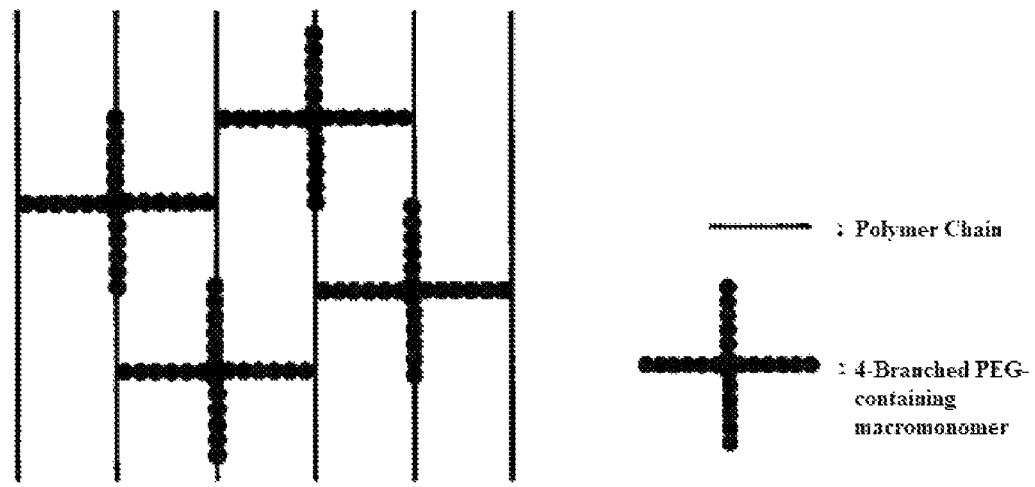
FIG. 2 is a simplified model diagram showing a polymer network formed when a macromonomer having a polyethylene glycol group in four branches is used.

On the other hand, a polymer obtained by using a macromonomer having a polyethylene glycol group in four branches (hereinafter, may be referred to as "4-branched PEG-containing macromonomer") tend to form a uniform network with less variation in distance between cross-linking points (refer to FIG. 2). In this way, it is assumed that the improvement on the uniformity of the network structure of the polymer contributes to the suppression of the occurrence of glistening and sub-surface nano glistening.

The differences in physical properties caused by the structure of the polymer also apply to the glass transition temperature of the polymer. Usually, the cross-link density of a polymer becomes higher as the usage amount of cross-linking agent increases. As a result, the freedom of mobility of the polymer chains is inhibited, leading to a higher glass transition temperature of the polymer.

Here, since the polyethylene glycol group has a highly flexible structure, a homopolymer composed of 2-branched PEG-containing macromonomers has a low glass transition temperature. However, even if the 2-branched PEG-containing macromonomers are used, the structure of the obtained polymer also becomes non-uniform as mentioned above. Therefore, the freedom of mobility of the polymer chains is inhibited, and the glass transition temperature cannot be greatly lowered. The tendency also exists in the 3-branched and 8-branched PEG-containing macromonomers.

On the other hand, since the 4-branched PEG-containing macromonomer tends to form a uniform network, the obtained polymer is less likely to inhibit the freedom of mobility of the polymer chains, and shows obvious flexibility in virtue of the flexibility of the polyethylene glycol group. Therefore, compared with the use of the 2-branched PEG-containing macromonomer, use of the 4-branched PEG-containing macromonomer can greatly reduce the

[Chemical Formula 10]

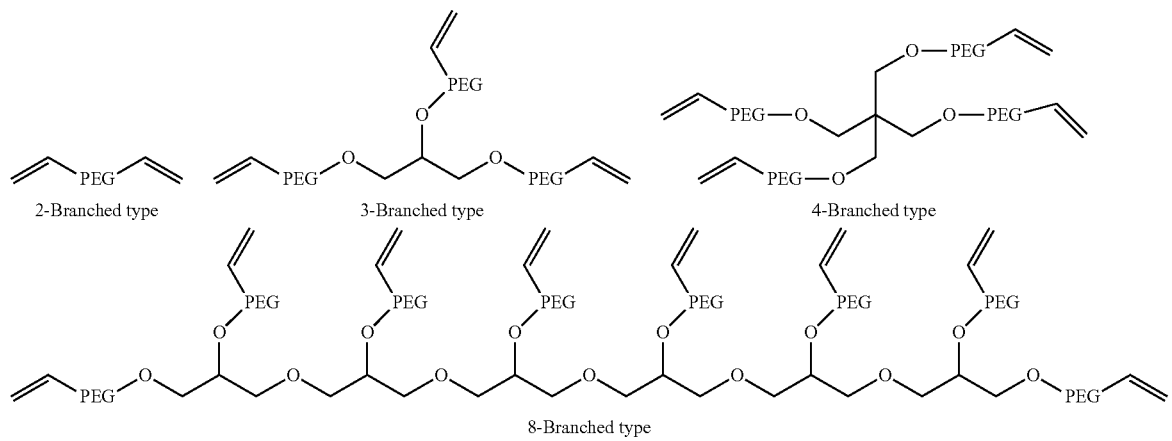

For example, a polymer obtained by using a macromonomer having a polyethylene glycol group in two branches (hereinafter, may be referred to as "2-branched PEG-conglass transition temperature and can also adjust the glass transition temperature of the polymer according to the usage amount.

Thus, compared with the usage amount of the 2-branched PEG-containing macromonomer, the usage amount of the 4-branched PEG-containing macromonomer can be less to reduce the glass transition temperature of the polymer. However, since the polyethylene glycol group is a factor to cause the decrease in the refractive index of the intraocular lens material, although it is preferably used in a small amount, use of the 4-branched PEG-containing macromonomer can reduce its usage amount to constrain the decrease in the refractive index of the intraocular lens material. In addition, reduction in the usage amount of the 4-branched PEG-containing macromonomer can lead to an increase in the usage amount of the (meth)acrylate monomer (B) described later, and consequently, can result in an increase in the refractive index of the intraocular lens material.

Furthermore, previously, the usage amount of the acrylate monomer having an aryl group, which is used as a component of the intraocular lens material, can be increased to impart flexibility to the polymer. Under such circumstances, use of the acrylate monomer leads to an increase in the adhesion of the intraocular lens material. On the contrary, in the invention, use of the 4-branched PEG-containing macromonomer can greatly reduce the glass transition temperature (flexibility) of the intraocular lens material. Therefore, the intraocular lens material of the invention is different from conventional intraocular lens materials in that the acrylate monomer having an aryl group is not used or used in a smaller amount and thus the usage amount of methacrylate monomer can be relatively increased, resulting in suppression of the increase in the adhesion of the obtained intraocular lens material.

In addition, the 4-branched PEG-containing macromonomer (macromonomer (A)) not only has the effects of suppressing the adhesion of the intraocular lens material while imparting flexibility and suppressing the occurrence of glistening and sub-surface nano glistening, but also functions as a cross-linking agent to exhibit an effect of improving the mechanical strength of the polymer (intraocular lens material).

The usage amount (content) of the macromonomer (A) may be about 11-30% by mass, preferably about 12-25% by mass, and more preferably about 13-20% by mass.

If the usage amount of the macromonomer (A) is less than the above-mentioned lower limit, the effect of suppressing the occurrence of glistening and sub-surface nano glistening of the intraocular lens material is not sufficiently obtained. On the other hand, if the usage amount of the macromonomer (A) exceeds the above-mentioned upper limit, the refractive index of the intraocular lens material is extremely reduced. In addition, since the number of cross-linking points increases, the intraocular lens material becomes brittle.

In addition, when expressed in mol %, the usage amount of the macromonomer (A) is about 1.2-5 mol %, preferably about 1.2-4 mol %, and more preferably about 1.2-3 mol %.

In addition, "percent by mass" refers to a value calculated on the basis of the total (100% by mass) of the mass of, in addition to the mass of the macromonomer (A) and the mass of the (meth)acrylate monomer (B) described below, a (meth)acrylate monomer (C) without having an aryl group, which serves as an optional component, and a cross-linking monomer (D).

Similarly, "mole percent" also refers to a value calculated on the basis of the total (100 mole %) of the mole number of the macromonomer (A), the mole number of the (meth) acrylate monomer (B), the mole number of the (meth)acrylate monomer (C) and the mole number of the cross-linking monomer (D).

<<(Meth)Acrylate Monomer (B)>>

The (meth)acrylate monomer (B) is a monomer having an aryl group and a (meth)acryloyl group. The (meth)acrylate monomer (B) exhibits an action of improving the refractive index of the obtained intraocular lens material.

The (meth)acrylate monomer (B) is preferably a monomer represented by a formula (II) below.

[Chemical Formula 11]

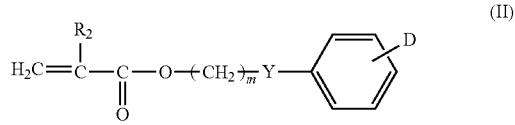

[In the formula, $R_2$ is a hydrogen atom or a methyl group; m is an integer from 1 to 6; Y is a direct bond or an oxygen atom; and D is a hydrogen atom, $-C_6H_5$, $-CH_2C_6H_5$ or $-OC_6H_5$.]

Specific examples of the (meth)acrylate monomer (B) include 2-phenylethyl (meth)acrylate, 3-phenylpropyl (meth)acrylate, 4-phenylbutyl (meth)acrylate, 2-phenoxyethyl (meth)acrylate, 4-phenoxybutyl (meth)acrylate, 2-(4-phenylphenyl)ethyl (meth)acrylate, 2-(3-phenylphenyl) ethyl (meth)acrylate, 2-(4-benzylphenyl)ethyl (meth) acrylate, 2-(4-phenylphenoxy)ethyl (meth)acrylate, 2-(4-benzylphenoxy)ethyl (meth)acrylate, 3-(4-phenylphenoxy) propyl (meth)acrylate, 2-(4-phenoxyphenoxy) ethyl (meth) acrylate, and the like. These monomers may be used alone or in combination of two or more.

Among them, the (meth)acrylate monomer (B) is preferably at least one selected from the group consisting of 2-phenoxyethyl methacrylate, 2-phenoxyethyl acrylate, 2-phenylethyl methacrylate, and 2-phenylethyl acrylate, and more preferably the combination of 2-phenoxyethyl methacrylate and 2-phenylethyl acrylate or the combination of 2-phenylethyl methacrylate, and 2-phenylethyl acrylate. By using the above (meth)acrylate monomer (B), the glass transition temperature of the intraocular lens material can be further reduced.

The usage amount (content) of the (meth)acrylate monomer (B) is not particularly limited, but it is preferably about 70 to 89% by mass, more preferably about 75 to 88% by mass, and still more preferably about 77 to 87% by mass.

By setting the usage amount of the (meth)acrylate monomer (B) in the above range, the refractive index of the intraocular lens material can be sufficiently increased, and the decrease in the flexibility of the intraocular lens material can be suppressed.

In addition, when the usage amount of the (meth)acrylate monomer (B) is expressed in mol %, it is preferably 85-98.8 mol %, more preferably 87-98.8 mol %, and still more preferably 90-98.8 mol %.

The liquid monomer mixture may also contain other monomers (C) to (F) and the like other than the macromonomer (A) and the (meth)acrylate monomer (B).

<<(Meth)Acrylate Monomer (C)>>

The (meth)acrylate monomer (C) is a monomer having no aryl group but having a (meth)acryloyl group. The (meth) acrylate monomer (C) is one of auxiliary monomers blended in the liquid monomer mixture for the purpose of adjusting the flexibility and/or water absorption rate of the intraocular lens material.

The (meth)acrylate monomer (C) is preferably a monomer represented by a formula (III) below.

[Chemical Formula 12]

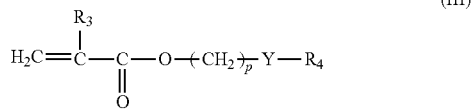

(III)

[In the formula, $R_3$ is a hydrogen atom or a methyl group; p is an integer from 0 to 4; Y is a direct bond or an oxygen atom; $R_4$ is a hydrogen atom, a linear or branched $C_1$-$C_8$ alkyl group, or a linear or branched $C_1$-$C_8$ alkyl group that may be substituted by a fluorine atom.]

Specific examples of the (meth)acrylate monomer (C) include 2-hydroxyethyl (meth)acrylate, 2-hydroxypropyl (meth)acrylate, 4-hydroxybutyl (meth)acrylate, methyl (meth)acrylate, ethyl (meth)acrylate, n-propyl (meth)acrylate, isopropyl (meth)acrylate, isobutyl (meth)acrylate, n-butyl (meth)acrylate, tert-butyl (meth)acrylate, isoamyl (meth)acrylate, hexyl (meth)acrylate, 2-ethylhexyl (meth)acrylate, 2-methoxyethyl (meth)acrylate, 2-ethoxyethyl (meth)acrylate, 2,2,2-trifluoroethyl (meth)acrylate, 2,2,3,3-tetrafluoropropyl (meth)acrylate, 2,2,3,3,3-pentafluoropropyl (meth)acrylate, 1,1,1,3,3,3-hexafluoroisopropyl (meth)acrylate, octafluoropentyl (meth)acrylate, and the like. These monomers may be used alone or in combination of two or more.

<<Cross-Linking Monomer (D)>>

The cross-linking monomer (D) is one of auxiliary monomers blended in the liquid monomer mixture for the purpose of adjusting the mechanical strength of the intraocular lens material.

Specific examples of the cross-linking monomer (D) include ethylene glycol di(meth)acrylate, diethylene glycol di(meth)acrylate, triethylene glycol di(meth)acrylate, tetraethylene glycol di(meth)acrylate, 1,3-propanediol di(meth)acrylate, 2,3-propanediol di(meth)acrylate, 1,4-butanediol di(meth)acrylate, 1,6-hexanediol di(meth)acrylate, 1,9-nonanediol di(meth)acrylate, neopentyl glycol di(meth)acrylate, glycerol di(meth)acrylate, 3-methyl-1,5-pentanediol diacrylate, 2-hydroxy-3-acryloyloxypropyl (meth)acrylate, polyethylene glycol di(meth)acrylate, and the like. These monomers may be used alone or in combination of two or more.

The usage amount (content) in total of the (meth)acrylate monomer (C) and the cross-linking monomer (D) is preferably less than 10% by mass, more preferably about 0.1-9% by mass, and further preferably about 0.2-8% by mass.

By setting the total usage amount of these monomers in the above range, the usage amount of the (meth)acrylate monomer (B) can be maintained at a high level, and as a result, the refractive index of the intraocular lens material can be prevented from decreasing.

In addition, when the total amount of usage of the (meth)acrylate monomer (C) and the cross-linking monomer (D) is expressed in mol %, it is preferably less than 13 mol %, and more preferably about 0.02-11 mol %, further preferably about 0.04-8 mol %.

<<Ultraviolet-Absorbing Polymerizable Monomer (E), Polymerizable Dye Monomer (F)>>

The polymerizable monomer (E) has a structure capable of absorbing ultraviolet light, and is blended in the liquid monomer mixture for the purpose of imparting an ultraviolet absorption capability to the intraocular lens (intraocular lens material).

Specific examples of the polymerizable monomer (E) include 5-chloro-2-[2-hydroxy-5-(D-methacryloyloxyethyl-carbamoyloxyethyl)]phenyl-2H-benzotriazole, 2-[2-hydroxy-5-(0-methacryloyloxyethylcarbamoyloxyethyl)]phenyl-2H-benzotriazole, 5-chloro-2-[2-hydroxy-4-(p-vinylbenzyloxy-2-hydroxypropyloxy)]phenyl-2H-benzotriazole, 4-methacryloxy-2-hydroxybenzophenone, 2-(2'-hydroxy-3'-tert-butyl-5'-methylphenyl)-5-(2'-methacryloyloxyethyl)benzotriazole, 2-(2'-hydroxy-5'-methacryloxyethylphenyl)-2H-benzotriazole, 2-(2'-hydroxy-3'-methallyl-5'-methylphenyl)benzotriazole, 2-(2-hydroxy-3-(methacryloxyaminomethyl)-5-tert-octylphenyl)-2H-benzotriazole, 2-(2'-hydroxy-3'-tert-butyl-5'-methylphenyl)-5-(2'-methacryloyloxyethyl)benzotriazole, 2-[3'-tert-butyl-2'-hydroxy-5'-(3"-methacryloyloxypropyl)phenyl]-5-methoxybenzotriazole, and the like. These monomers may be used alone or in combination of two or more.

The polymerizable monomer (F) has, for example, a structure in yellow capable of absorbing blue light, and is blended in the liquid monomer mixture for the purpose of dyeing the intraocular lens.

The polymerizable monomer (F) may use azo-based, pyrazolone-based, and cyanine-based yellow colorants. Specific examples include yellow colorants disclosed in Japanese Patent Application Laid-Open No. 10-195324, Japanese Patent Application Laid-Open No. 2000-290256, Japanese Patent Application Laid-Open No. 2003-119226, Japanese Patent Application No. 2008-520811, Japanese Patent Application No. 2008-520352, Japanese Patent Application No. 2012-532244, and the like, the entire contents of which are incorporated herein by reference.

The usage amount (content) of the polymerizable monomer (E) relative to the total amount (100% by mass) of the mass of the monomers (A) to (D) is preferably 5% by mass or less and more preferably about 0.1-3% by mass.

In addition, the usage amount (content) of the polymerizable monomer (F) relative to the total amount (100% by mass) of the mass of the monomers (A) to (D) is preferably 1% by mass or less and more preferably about 0.01-0.5% by mass.

The macromonomer (A), the (meth)acrylate monomer (B), the monomers (C) to (F) as required, and a polymerization initiator (G) are mixed and sufficiently stirred to obtain a homogeneous liquid monomer mixture.

<<Polymerization Initiator (G)>>

The polymerization initiator (G) may use either of a thermal polymerization initiator and a photopolymerization initiator.

Examples of thermal polymerization initiators include: peroxides, such as di(3,5,5-trimethylhexanoyl)peroxide, dilauroyl peroxide, benzoyl peroxide, tert-hexyl peroxy-2-ethylhexanoate, 1,1,3,3-tetramethylbutyl peroxy-2-ethylhexanoate, and tert-butyl peroxy-2-ethylhexanoate; 2,2'-azobis(2,4-dimethylvaleronitrile); 2,2'-azobis(isobutyronitrile); dimethyl-2,2'-azobis(2-methylpropionate); 2,2'-azobis(2-methylbutyronitrile); dimethyl-1,1'-azobis(1-cyclohexanecarboxylate); 1,1'-azobis(cyclohexane-1-carbonitrile); and the like.

Examples of the photopolymerization initiator include benzoin methyl ether, 1-hydroxycyclohexyl phenyl ketone, 2,2-dimethoxy-2-phenylacetophenone, 2-hydroxy-2-dimethoxy-1-phenylpropane-1-one, phenylbis(2,4,6-trimethylbenzoyl)phosphine oxide, 2,4,6-trimethylbenzoyl-diphenylphosphine oxide, and the like.

The usage amount (content) of the polymerization initiator (G) is appropriately selected according to the polymerization temperature, the irradiation wavelength of light, the irradiation intensity, and the like, but it is preferably about 0.1-1% by mass relative to the total amount (100% by mass) of the mass of the monomers (A) to (D).

<Intraocular Lens>

The liquid monomer mixture is injected into an injection mold for produce an intraocular lens having a shape corresponding to the shape of the intraocular lens to be produced, and then polymerized.

This injection mold is a combined mold in which curved recesses are formed, and is composed of a material such as metal and resin. The material preferably ensures the polymer (the intraocular lens material or the intraocular lens) of the liquid monomer mixture to have good releasability excellent solvent resistance and heat resistance. A resin injection mold can be easily formed into a shape required for a desired lens design, so it is preferable.

The resin material is preferably selected from materials having low mold shrinkage, good transferability from the surface of the metal material, and excellent dimensional accuracy and solvent resistance. In particular, polypropylene is preferred as the resin material from the viewpoints of inexpensiveness and availability.

However, the resin material is not limited to polypropylene. For example, polyethylene, polyethylene terephthalate, polymethylpentene, polysulfone, polyphenylene sulfide, cyclic olefin copolymers, and ethylene-vinyl alcohol copolymers, and the like may also be used.

To inject the liquid monomer mixture, an injection mold immediately after formation may be used. In order to stabilize the shape (curvature) of the curved recesses, an injection mold stored for about 10 to 72 hours may be used.

In addition, before using the injection mold, the pressure may be well reduced to remove substances that affect the polymerization reaction, such as moisture and oxygen on the surface of the mold. Furthermore, after the injection mold is purged with an inert gas such as nitrogen and argon, the liquid monomer mixture may be injected into the injection mold.

Furthermore, during injection, the liquid monomer mixture may be pre-bubbled with an inert gas such as nitrogen and argon to remove oxygen dissolved therein before use. Alternatively, the liquid monomer mixture may be used without removal of the dissolved oxygen.

Examples of the polymerization method include: a thermal polymerization method in which the liquid monomer mixture is mixed with a thermal polymerization initiator to be heated; a photopolymerization method in which the liquid monomer mixture is mixed with a photopolymerization initiator, and then irradiated with ultraviolet light, visible light, or the like.

When the thermal polymerization method is applied, the injection mold is placed in a polymerization reactor, followed by heating for about 5-48 hours stepwise or continuously in the temperature range of about 20 to 130° C., or the injection mold may be placed in a polymerization reactor set at a predetermined temperature (about 100 to 120° C.) in advance and then heated for about 1 to 24 hours.

The atmosphere for thermal polymerization may be the atmospheric atmosphere, but is preferably an inert gas atmosphere, such as a nitrogen atmosphere and an argon atmosphere. Thermal polymerization in the above-mentioned atmosphere allows improvement in the polymerization rate of the monomer and reduction in the amount of unreacted monomer. In this case, the pressure in the polymerization reactor is preferably 2 kgf/cm$^2$ (0.196 MPa) or less.

When the photopolymerization method is applied, the wavelength of the irradiated light is appropriately selected according to the properties of the blended photopolymerization initiator, so there is not particularly limited.

In addition, specific examples of a lamp used for light irradiation include a lamp having a strong peak in the wavelength range of 200-280 nm and at the wavelength of 350 nm, a lamp with an enhanced wavelength in the range of 350-400 nm, a lamp that has an enhanced wavelength in the range of 400-425 nm centered on the wavelength of 420 nm, a lamp with an enhanced wavelength in the range of 400-450 nm, and the like.

The value of the intensity of light irradiation varies depending on the area of the light-receiving portion of a device that measures the irradiation intensity, but is preferably about 5 to 100 mW/cm$^2$, for example.

Since the time for light irradiation (polymerization time) is appropriately set according to the intensity of light irradiation, it is not particularly limited. For example, when the intensity of light irradiation is about 5 to 100 mW/cm$^2$, it is preferable to set the time for light irradiation to about 5 to 60 minutes.

In addition, for photopolymerization, light irradiation may be given in the polymerization reactor set in advance at a predetermined temperature (about 40 to 80° C.). Therefore, the polymerization rate of the monomer can be increased to reduce the amount of unreacted monomer.

The atmosphere for photopolymerization may be the atmospheric atmosphere, or an inert gas atmosphere, such as the nitrogen atmosphere and the argon atmosphere. Photopolymerization in the above-mentioned atmosphere allows further improvement in the polymerization rate of the monomer.

After polymerization of the liquid monomer mixture, the intraocular lens material is taken out of the injection mold or the intraocular lens material is not taken out of the injection mold (i.e., in a state where the intraocular lens material is stored in the injection mold), followed by cutting and polishing the intraocular lens material at low temperatures to be processed into a desired shape (for example, the shape of the intraocular lens itself and the shape of the optical portion of the intraocular lens) at a low temperature.

According to another method, polymerization of the liquid monomer mixture may also be carried out in a suitable mold or container to prepare an intraocular lens material in a predetermined shape, such as a rod, block, or plate shape, and subsequently, the intraocular lens material may be cut and polished at a low temperature processed into a desired shape.

The intraocular lens material may also be taken out of the injection mold and directly used as the intraocular lens itself or the optical part (lens body) of the intraocular lens without cutting or polishing.

In addition, when the optical part is manufactured, a support part to support the optical part may be manufactured separately from the optical part can be attached to the optical part to serve as an intraocular lens. In addition, the support part may be formed integrally with the optical part at the same time.

Examples of a material to compose the support part include polypropylene and polymethyl methacrylate (PMMA).

As described above, the intraocular lens of the invention is made of the intraocular lens material itself of a predetermined shape, or a product of processing the intraocular lens material.

Optionally, the intraocular lens (optical part) may also be subjected to reheating-based treatment after being obtained. Thereby, a small amount of unreacted monomers remaining in the intraocular lens and the like can be removed. The reheating-based treatment involves arranging the intraocular lens in a device set at a predetermined temperature (about 100 to 125° C.) in advance and heating for about 5 to 72 hours. The atmosphere in the device under such circumstance may be the atmospheric atmosphere, or an atmosphere with reduced pressure using a vacuum pump or the like (vacuum atmosphere).

Moreover, the small amount of unreacted monomers remaining in the intraocular lens may also be removed by the process of immersing the intraocular lens in an organic solvent, such as ethanol, isopropyl alcohol, or acetone, apart from the reheating-based treatment.

In addition, the surface of the optical part of the intraocular lens may also be subjected to low-temperature plasma treatment, atmospheric pressure plasma treatment, ultraviolet cleaning treatment, and the like. The treatment described above can enhance the cleanliness and cell adhesion of the surface of the optical part of the intraocular lens.

The refractive index of the intraocular lens material thus obtained is measured with an Abbe refractometer at 25° C. in the presence of e-rays (546.1 nm). The value of the refractive index in the state of saturated water absorption is preferably about 1.51 to 1.57, more preferably about 1.52 to 1.57, and further preferably about 1.525 to 1.57.

In addition, the water absorption rate of the intraocular lens material at 23° C. is preferably about 0.7 to 4.5% by mass, more preferably about 0.8 to 3% by mass, and further preferably about 0.9 to 2% by mass.

Furthermore, the intraocular lens material is used as a foldable intraocular lens at room temperature, so it is preferable to have a glass transition temperature lower than a normal human body temperature (about 37° C.). Specifically, the lower limit of the glass transition temperature of the intraocular lens material is preferably about 0° C., more preferably about 3° C., further preferably about 5° C., particularly preferably about 7° C., and most preferably about 10° C. On the other hand, the upper limit of the glass transition temperature is preferably about 20° C., more preferably about 18° C., further preferably about 17° C., further preferably about 15° C., and particularly preferably about 12° C. The glass transition temperature of the intraocular lens material may be about 10 to 15° C. from the viewpoint of obtaining the intraocular lens material with suitable shape recovery.

The intraocular lens material as described above has higher resistance to glistening and sub-surface nano glistening than conventional intraocular lens materials do. Here, glistening and sub-surface nano glistening are evaluated by the following procedure.

First, a lens-shaped or flat-plate shaped sample is immersed in physiological saline at 45° C. for 24 hours or more. Next, the sample after immersion is allowed to stand for 2 hours in an environment set at 23° C. Then, the appearance (transparency) of this sample is observed at 20 or more power using, for example, a microscope (manufactured by Keyence Corporation, "VHX-5000").

Herein, "glistening" refers to the situation where several to dozens of water particles with a particle size in a range of 1-10 μm are formed in the intraocular lens material while the transparency of the intraocular lens material does not substantially decrease. On the other hand, "sub-surface nano glistening" refers to the situation where the massive gathering of small water particles with an average particle size of 100 nm causes the surface of the intraocular lens material to appear foggy and white.

In addition, the evaluation of glistening and sub-surface nano glistening is carried out on the basis of the theory that a temperature change in the eye occurs in ophthalmic surgery in which the intraocular lens is actually inserted into the human eye or in living environment after the intraocular lens is inserted into the eye.

It is believed that such a temperature change in the body results in glistening and sub-surface nano glistening on the intraocular lens material. Generally, for intraocular lens materials with low water absorption, a higher temperature leads to higher water absorption rate. Therefore, it is understood that the evaluation of glistening and sub-surface nano glistening is carried out under more severe conditions when the temperature changes in a wider range (45° C. to 23° C.). According to the intraocular lens material of the invention, glistening and sub-surface nano glistening are not found even under the severe conditions described above.

The polymer material and the intraocular lens of the invention have been described above, but the invention is not limited to the configurations of the above-described embodiments.

For example, for the polymer material and the intraocular lens of the invention, other optional components may be added to the configurations of the above-described embodiments, or optional components that perform the same function may be used as replacements.

In addition to the intraocular lens, the polymer material of the invention can also be used to make various medical devices, for example: ophthalmic medical devices, such as corneal inlays and corneal rings; otorhinolaryngologic medical devices, such as otolaryngologic ventilation tubes and nasal implants.

EXAMPLES

The invention will be described in more detail below using Examples, but the invention is not limited to these Examples 1. Components Used The names and the abbreviations of the compounds used in the following Examples and Comparative Examples are shown.

(A) 4-Branched PEG-Containing Macromonomer

4-ArmPEG34:

The formula (A1) above represents a monomer having a polyethylene glycol group of which the number of repetitions (a, b, c, and d each) is 8 or 9 and the total of a, b, c, and d is 34 [molecular weight: 1846].

4-ArmPEG40:

The formula (A1) above represents a monomer having a polyethylene glycol group of which the number of repetitions (a, b, c, and d all) is 10 and the total of a, b, c, and d is 40 [molecular weight: 2112].

(B) (Meth)Acrylate Monomer with an Aryl Group

Po-MA:

2-phenoxyethyl methacrylate [molecular weight: 206]

Po-A:

2-phenoxyethyl acrylate [molecular weight: 192]

Ph-MA:

2-phenylethyl methacrylate [molecular weight: 190]

Ph-A:
2-phenylethyl acrylate [molecular weight: 176]
(C) (Meth)Acrylate Monomer without an Aryl Group
n-BuMA: n-butyl methacrylate [molecular weight: 142]
(D) Cross-Linking Monomer
PEG-1000A:
A formula (D1) below represents polyethylene glycol diacrylate [molecular weight: 1097].

[Chemical Formula 13]

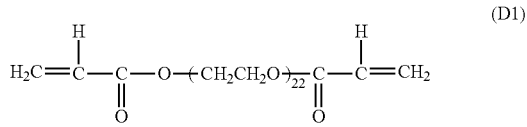

(D1)

TEGDMA:
Tetraethylene glycol dimethacrylate [molecular weight: 330]
(E) Ultraviolet-Absorbing Polymerizable Monomer
Norbloc7966:
2-(2'-hydroxy-5'-methacryloxyethylphenyl)-2H-benzotriazole [molecular weight: 323](F) Polymerizable dye monomer
BL01:
4-(phenyldiazenyl)phenyl-2-methacrylate [molecular weight: 266]
(G) Polymerization Initiator
AIBN:
2,2'-azobis(isobutyronitrile) [molecular weight: 164]
2. Production of the Intraocular Lens Material Example 1

First, Po-MA, Ph-A, 4-ArmPEG34, Norbloc7966, and AIBN were put into glass bottles with a volume of 10 mL in the following amounts, respectively, and stirred at room temperature for about 20 hours. Thus, a liquid monomer mixture was prepared.
Po-MA: 1.770 g (44.25% by mass, 45.47 mol %)
Ph-A: 1.770 g (44.25% by mass, 53.22 mol %)
4-ArmPEG34: 0.460 g (11.5% by mass, 1.32 mol %)
Norbloc7966: 0.060 g (1.5% by mass relative to the total mass of Po-MA, Ph-A, and 4-ArmPEG34)
AIBN: 0.012 g (0.3% by mass relative to the total mass of Po-MA, Ph-A, and 4-ArmPEG34)

Next, the liquid monomer mixture was injected into a cell for preparing the intraocular lens material. The cell was composed of two polypropylene plates, each plate cut into a size of 7.5 cm in length and 5.0 cm in width, and a polytetrafluoroethylene spacer sandwiched between the two plates to define a clearance therebetween.

Then, the cell injected with the liquid monomer mixture was placed in a polymerization reactor; the temperature was raised from 20° C. to 50° C. in 30 minutes, then maintained at 50° C. for 8 hours, followed by a further increase to 120° C. in 6 hours, and maintained at 120° C. for 2 hours; and finally, cooled to 40° C. in 4 hours. Thus, monomers contained in the liquid monomer mixture were polymerized. In addition, the atmosphere in the polymerization reactor was a nitrogen atmosphere, and the pressure in the apparatus was 0.2 kgf/cm² (0.0196 MPa).

Next, the obtained intraocular lens material was placed in an oven set at 120° C. in advance, and subjected to heat treatment for 8 hours. Thus, unreacted monomers were removed from the intraocular lens material. In addition, the thickness of the obtained flat-shaped intraocular lens material was in the range from 0.6 to 0.7 mm.

Examples 2, 3

Except for preparing the liquid monomer mixture of the composition shown in Table 1, intraocular lens materials were produced in the same manner as Example 1 above.

Examples 4-6

Except for preparing the liquid monomer mixture of the composition shown in Table 2, intraocular lens materials were also produced in the same manner as Example 1 above.

Examples 7-13

Except for preparing the liquid monomer mixture of the composition as shown in Table 3, intraocular lens materials were also produced in the same manner as Example 1 above.

Comparative Examples 1-6

Except for preparing the liquid monomer mixture of the composition as shown in Table 1, intraocular lens materials were also produced in the same manner as Example 1 above.

Comparative Example 7

In addition to the mixed monomer solution as shown in Table 3, an intraocular lens material was also produced in the same manner as Example 1 above.

3. Measurement and Evaluation

The refractive index, the water absorption rate, and the glass transition temperature of the intraocular lens material obtained in each Example and Comparative Example were measured, and their adhesion and glistening and sub-surface nano glistening were evaluated.

During measurement of the refractive index, the intraocular lens material cut into a rectangular shape with a width of 10 mm and a length of 15 mm was used as a test piece.

In addition, during the measurement of the glass transition temperature, the intraocular lens material punched into a round disk shape through a p 5 mm biopsy punch was used as a test piece.

Thus, during other measurement and evaluation, the intraocular lens materials punched in a size equivalent to the optical part (lens body) of the intraocular lens through a p 6 mm biopsy punch were used as test pieces.

3-1. Measurement of the Refractive Index

The test piece was immersed in physiological saline at 25° C. for 72 hours to be saturated with absorbed water. The refractive index of the test piece was measured with a refractometer (manufactured by ATAGO Corporation, DR-M2) at 25° C. in the presence of e-rays (546.1 nm).

3-2. Measurement of the Water Absorption Rate

The weight (Ww) of the test piece which was saturated with absorbed water at 23° C. and the weight (Wd) of the test piece after 4 hours drying in a reduced-pressure vacuum oven at 60° C. (vacuum degree: 266.6 Pa) were measured, and the water absorption rate was calculated using the following formula.

Water absorption rate (mass %)={($Ww-Wd$)/$Wd$}× 100 Formula:

3-3. Evaluation of the Adhesion

The test piece was folded double and held for 1 min using tweezers. Then, the state of the test piece released from the tweezers was visually observed and evaluated in accordance with the following evaluation standard.

<Evaluation Standard>
G (Good): The test piece folded double did not fit, but quickly recovered to its original shape.
B (Bad): The test piece folded double fit and it took time to start recovery to its original shape.

3-4. Evaluation of Glistening and Sub-Surface Nano Glistening

The test piece was immersed in physiological saline at 45° C. for 48 hours and then allowed to stand for 2 hours in an environment set at 23° C. Then, the appearance (transparency) of the test piece in the physiological saline was observed at 50 power using a microscope (manufactured by Keyence Corporation, "VHX-5000") and evaluated with reference to the following evaluation standard.

<Evaluation Standard>
G (Good): The test piece had excellent transparency, and no water particles were found therein.
B (Bad): The test piece appeared opaque (sub-surface nano glistening) or water particles were found therein (glistening) even though the test piece was transparent.

3-5. Measurement of the Glass Transition Temperature

The glass transition temperature (Tg) of the test piece (dry) was measured as described below using a differential scanning calorimeter. First, the test piece was temporarily heated to a temperature of the glass transition temperature or higher; after imparting a certain thermal hysteresis, the test piece was cooled to −20° C. at the speed of 10° C./min; then, the temperature was again raised from −20° C. to 50° C. at the same speed of 10° C./min. A heat flux curve was drawn through the acquired data, and the midpoint in the transition region thereof was determined as the glass transition temperature.

The obtained results were shown in Tables 1-3 below and FIGS. 3-5.

In the Table, the usage amount of each component was expressed in % by mass. In addition, the usage amounts of the components (E), (F), and (G) were respectively expressed in ratio to the total mass (100% by mass) of the components (A), (B), (C), and (D).

In addition, "*" was expressed in ratio to the total mole number of the components (A), (B), (C), and (D).

Figure 3:
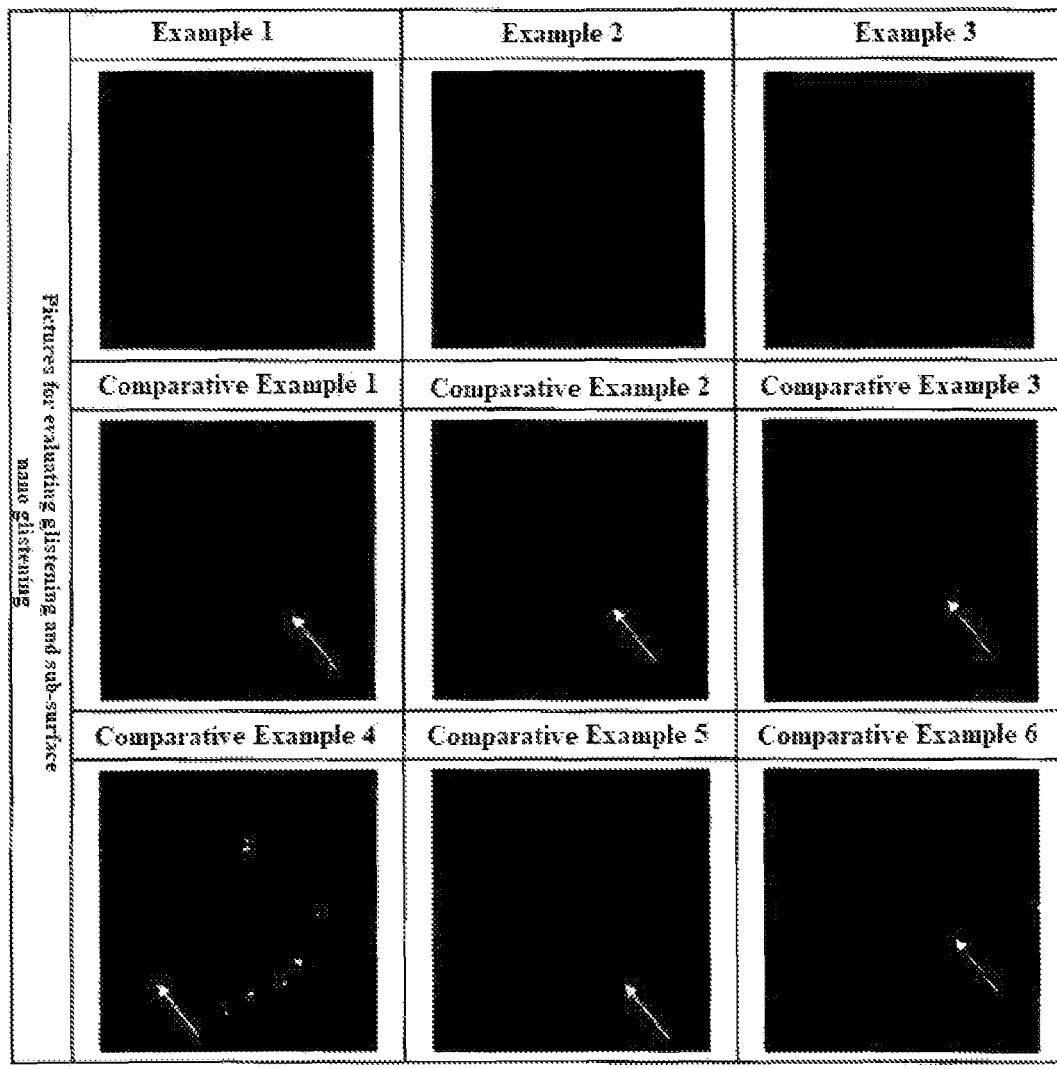
FIG. 3 shows pictures used for evaluating glistening and sub-surface nano glistening.

As shown in Table 1 and FIG. 3, the refractive indexes of the intraocular lens materials obtained in Examples 1-3 were respectively 1.548, 1.543, and 1.535, and no adhesion and no glistening and sub-surface nano glistening were found.

On the contrary, in Comparative Examples 1 and 2 in which the usage amounts of the 4-branched PEG-containing macromonomer (A) were 10% by mass or less, the obtained intraocular lens materials both had foggy opaque surfaces showing the sub-surface nano glistening. In addition, according to the arrows in FIG. 3, the presence of numerous water particles was found. Similarly, the intraocular lens material obtained in Comparative Example 3 was transparent, but according to the arrow in FIG. 3, the presence of numerous water particles was found therein showing the glistening.

In addition, for the intraocular lens materials obtained in Comparative Examples 4-6 in which the 2-branched PEG-containing macromonomer was used to replace the 4-branched PEG-containing macromonomer (A), the usage amounts of the 2-branched PEG-containing macromonomer (PEG-1000A) were substantially the same as those of the 4-branched PEG-containing macromonomer (A) (4-Arm-PEG34) in mol %. However, the intraocular lens materials obtained in Comparative Examples 4 and 5 had foggy opaque surfaces showing the sub-surface nano glistening. In addition, according to the arrows in FIG. 3, the presence of numerous water particles was also found. Similarly, the intraocular lens material obtained in Comparative Example 6 was transparent, but according to the arrow in FIG. 3, the presence of numerous water particles was found therein showing the glistening.

TABLE 1

| Component | Abbreviation | Comparative Example 1 | Comparative Example 2 | Comparative Example 3 | Example 1 | Example 2 | Example 3 | Comparative Example 4 | Comparative Example 5 | Comparative Example 6 |
|---|---|---|---|---|---|---|---|---|---|---|
| (A) | 4-ArmPEG34 | 3.8 | 8 | 10 | 11.5 | 15.3 | 20 | | | |
|  | 4-ArmPEG40 | | | | | | | | | |
| (B) | Po-MA | 48.1 | 46 | 45 | 44.25 | 42.35 | 40 | 46.43 | 45.15 | 43.5 |
|  | Po-A | | | | | | | | | |
|  | Ph-MA | | | | | | | | | |
|  | Ph-A | 48.1 | 46 | 45 | 44.25 | 42.35 | 40 | 46.43 | 45.15 | 43.5 |
| (C) | n-BuMA | | | | | | | | | |
| (D) | PEG-1000A | | | | | | | 7.14 | 9.7 | 13 |
|  | TEGDMA | | | | | | | | | |
| (E) | Norbloc7966 | 1.5 | 1.5 | 1.5 | 1.5 | 1.5 | 1.5 | 1.5 | 1.5 | 1.5 |
| (F) | BL01 | | | | | | | | | |
| (G) | AIBN | 0.3 | 0.3 | 0.3 | 0.3 | 0.3 | 0.3 | 0.3 | 0.3 | 0.3 |
| Mol % of the component (A)* | | 0.40 | 0.89 | 1.13 | 1.32 | 1.82 | 2.51 | — | — | — |
| Mol % of the component (B)* | | 99.60 | 99.11 | 98.87 | 98.68 | 98.18 | 97.49 | 98.69 | 98.18 | 97.48 |
| Mol % of the component (C) and (D)* | | — | — | — | — | — | — | 1.31 | 1.82 | 2.52 |
| Refractive index | | 1.559 | 1.554 | 1.552 | 1.548 | 1.543 | 1.535 | — | — | — |
| Water absorption rate (%) | | 0.49 | 0.56 | 0.78 | 1.01 | 1.23 | 1.53 | 0.84 | 0.96 | 1.65 |
| Adhesion | | G | G | G | G | G | G | G | G | G |
| Glistening and sub-surface nano glistening | | B | B | B | G | G | G | B | B | B |
| Glass transition temperature (° C.) | | 17.7 | 13.6 | 12.1 | 10.6 | 5.6 | 3.2 | 14.9 | 12.2 | 8.8 |

Here, one molecule of 4-ArmPEG34 contained 34 ethylene oxide groups (—CH$_2$CH$_2$O—). Since the ethylene oxide group had a molecular weight of 44, it was calculated that the polyethylene glycol groups accounted for 81.04% in one molecule of 4-ArmPEG34 (∵44×34÷1846×100=81.04%).

Similarly, since one molecule of PEG-1000A contained 22 ethylene oxide groups, it was calculated that the polyethylene glycol groups accounted for 88.24% in one molecule of PEG-100A (∵44×22÷1097×100=88.24%).

Thus, in terms of the ratio of the polyethylene glycol groups in the intraocular lens material, although the ratio in PEG-1000A was higher than that in 4-ArmPEG34, the intraocular lens materials obtained in Comparative Examples 4-6 still showed glistening and sub-surface nano glistening. This indicates that the 4-branched structure of the macromonomer contributes to the suppression of the occurrence of glistening and sub-surface nano glistening.

Figure 4:
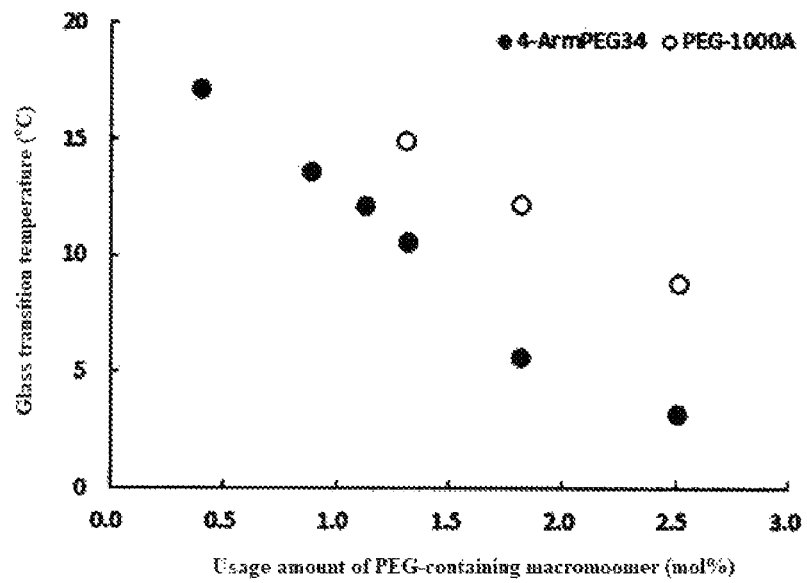
FIG. 4 is a graph showing the relationship between the usage amount of the macromonomer having a polyethylene glycol group in two branches and in four branches and the glass transition temperature of the intraocular lens material (Examples 1-3 and Comparative Examples 1-6).

FIG. 4 shows a graph of plotting the usage amounts (mol %) of 4-ArmPEG34 (Examples 1-3, Comparative Examples 1-3) and the usage amounts (mol %) of PEG-1000A (Comparative Examples 4-6) on the abscissa and the glass transition temperature of the intraocular lens material on the ordinate.

From FIG. 4, it is clearly understood that the usage amount of 4-ArmPEG34 and the glass transition temperature of the intraocular lens material show a good linear relationship. From the results, it is clearly understood that the glass transition temperature of the intraocular lens material can be changed simply by various adjusting the usage amount of 4-ArmPEG34.

In addition, the ratio of the decrease in the glass transition temperature of the intraocular lens material containing 4-ArmPEG34 was bigger than that of the intraocular lens material containing PEG-1000A. It is believed that such result was obtained because 4-ArmPEG34 is easier to form a more uniform network than PEG-1000A is, causing the polymer chains to have a degree of freedom of mobility less likely to be inhibited, and therefore results in apparent reflection of the flexibility of the polyethylene glycol group.

Therefore, since a smaller amount of 4-ArmPEG34 used can reduce the glass transition temperature of the intraocular lens material, a more amount of the (meth)acrylate monomer (B) having an aryl group can be used, and as a result, the intraocular lens material with a high refractive index can be provided.

TABLE 2

| Component | Abbreviation | Example4 | Example5 | Example6 |
|---|---|---|---|---|
| (A) | 4-ArmPEG34 | 11.5 | 15.3 | 20 |
|  | 4-ArmPEG40 |  |  |  |
| (B) | Po-MA |  |  |  |
|  | Po-A |  |  |  |
|  | Ph-MA | 53.1 | 50.8 | 48 |
|  | Ph-A | 35.4 | 33.9 | 32 |
| (C) | n-BuMA |  |  |  |
| (D) | PEG-1000A |  |  |  |
|  | TEGDMA |  |  |  |
| (E) | Norbloc7966 | 1.5 | 1.5 | 1.5 |
| (F) | BL01 | 0.02 | 0.02 | 0.02 |
| (G) | AIBN | 0.3 | 0.3 | 0.3 |
| Mol % of the component (A)* |  | 1.28 | 1.77 | 2.43 |
| Mol % of the component (B)* |  | 98.72 | 98.23 | 97.57 |
| Mol % of the component (C) and (D)* |  | — | — | — |
| Refractive index |  | 1.548 | 1.541 | 1.534 |
| Water absorption rate (%) |  | 0.86 | 1.51 | 1.85 |
| Adhesion |  | G | G | G |
| Glistening and sub-surface nano glistening |  | G | G | G |
| Glass transition temperature (° C.) |  | 12.4 | 10.5 | 8.8 |

In the Table, the usage amount of each component was expressed in % by mass. In addition, the usage amounts of the components (E), (F), and (G) were respectively expressed in ratio to the total mass (100% by mass) of the components (A), (B), (C), and (D).

In addition, "*" was expressed in ratio to the total mole number of the components (A), (B), (C), and (D).

The intraocular lens materials obtained in Examples 4-6 were dyed yellow by using BL01 as the polymerizable monomer (F). In addition, as shown in Table 2, the intraocular lens materials obtained in Examples 4-6 did not show adhesion and did not develop glistening and sub-surface nano glistening.

Figure 5:
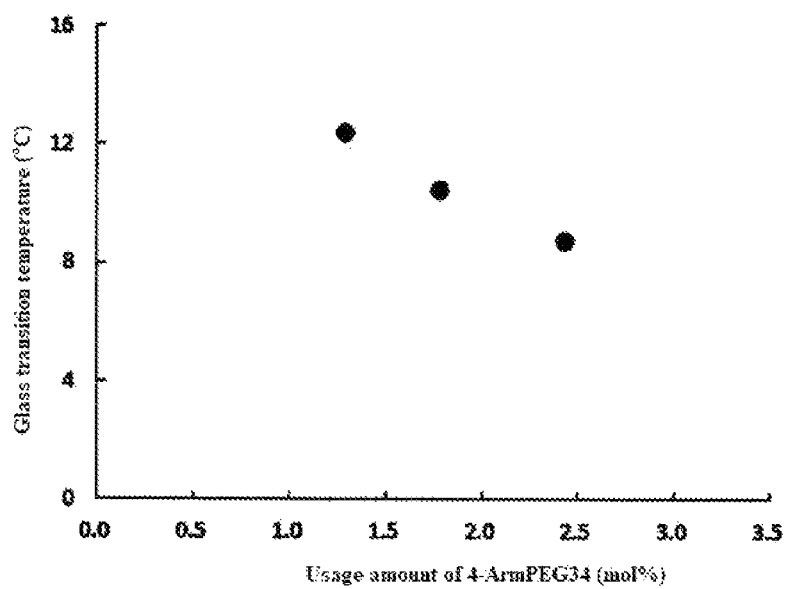
FIG. 5 is a graph showing the relationship between the usage amount of the macromonomer having a polyethylene glycol group in four branches and the glass transition temperature of the intraocular lens material (Examples 4-6).

FIG. 5 shows a graph of plotting the usage amounts (mol %) of 4-ArmPEG34 (Examples 4-6) on the abscissa and the glass transition temperature of the intraocular lens material on the ordinate.

From FIG. 5, it is clearly understood that the usage amount of 4-ArmPEG34 and the glass transition temperature of the intraocular lens material show a good linear relationship, and the correlation between the usage amount of 4-ArmPEG34 and the glass transition temperature of the intraocular lens material was found.

TABLE 3

| Component | Abbreviation | Example 7 | Example 8 | Example 9 | Example 10 | Example 11 | Example 12 | Example 13 | Comparative Example 7 |
|---|---|---|---|---|---|---|---|---|---|
| (A) | 4-ArmPEG34 | 15.3 | 30 | 25 | 28 | 13 |  |  | 7.4 |
|  | 4-ArmPEG40 |  |  |  |  |  | 15 | 20 |  |
| (B) | Po-MA | 33.9 | 70 |  |  |  | 42.5 | 40 |  |
|  | Po-A | 50.8 |  |  |  |  |  |  | 46.3 |
|  | Ph-MA |  |  | 75 | 72 | 60.9 |  |  |  |
|  | Ph-A |  |  |  |  | 21.8 | 42.5 | 40 |  |
| (C) | n-BuMA |  |  |  |  | 4 |  |  | 46.3 |
| (D) | PEG-1000A |  |  |  |  |  |  |  |  |
|  | TEGDMA |  |  |  |  | 0.3 |  |  |  |
| (E) | Norbloc7966 | 1.5 | 1.5 | 1.5 | 1.5 | 1.5 | 1.5 | 1.5 | 1.5 |
| (F) | BL01 |  |  |  |  |  |  |  |  |
| (G) | AIBN | 0.3 | 0.3 | 0.3 | 0.3 | 0.3 | 0.3 | 0.3 | 0.3 |

TABLE 3-continued

| Component | Abbreviation | Example 7 | Example 8 | Example 9 | Example 10 | Example 11 | Example 12 | Example 13 | Comparative Example 7 |
|---|---|---|---|---|---|---|---|---|---|
| Mol % of the component (A)* | | 1.89 | 4.56 | 3.32 | 3.85 | 1.47 | 1.52 | 2.13 | 0.70 |
| Mol % of the component (B)* | | 98.11 | 95.44 | 96.68 | 96.15 | 92.48 | 98.48 | 97.87 | 42.22 |
| Mol % of the component (C) and (D)* | | — | — | — | — | 6.05 | — | — | 57.08 |
| Refractive index | | 1.542 | 1.523 | 1.531 | 1.526 | 1.527 | 1.543 | 1.540 | — |
| Water absorption rate (%) | | 1.50 | 4.16 | 2.94 | 3.22 | 1.05 | 1.07 | 1.30 | — |
| Adhesion | | G | G | G | G | G | G | G | B |
| Glistening and sub-surface nano glistening | | G | G | G | G | G | G | G | B |
| Glass transition temperature (° C.) | | 7.6 | 16.3 | 16.9 | 16.5 | 15.5 | 9.8 | 5.7 | — |

In the Table, the usage amount of each component was expressed in % by mass. In addition, the usage amounts of the components (E), (F), and (G) were respectively expressed in ratio to the total mass (100% by mass) of the components (A), (B), (C), and (D).

In addition, "*" was expressed in ratio to the total mole number of the components (A), (B), (C), and (D).

As shown in FIG. 3, any of the intraocular lens materials obtained in Examples 7-13 did not show adhesion and did not develop glistening and sub-surface nano glistening.

On the contrary, the intraocular lens material obtained in Comparative Example 7 showed adhesion, and the surfaces of the optical parts were fit. In addition, the intraocular lens material obtained in Comparative Example 7 had a foggy opaque surface showing the sub-surface nano glistening.

In addition, when the monomers that were expressed by the formulas (A2)-(A4) as above and of which the number of repetitions (a, b, c, and d) of the polyethylene glycol group was 8 or 9 and the total of a, b, c, and d was 34 were used as the 4-branched PET-containing macromonomer (A) to produce the intraocular lens material in the same way as Examples 1-13, the results exhibiting similar tendencies to Examples 1-13 above were obtained.

Therefore, when the (meth)acrylate monomers (B) having different kinds of aryl groups as described above were used to produce the intraocular lens materials in the same way as Examples 1-13, the obtained results were similar to those obtained by Examples 1-13, the results exhibiting similar tendencies to Examples 1-13 above were obtained.

What is claimed is:

1. A polymer material, formed by polymerizing a liquid monomer mixture comprising:

a macromonomer (A) represented by the following formula (I); and a (meth)acrylate monomer (B) with an aryl group, and optionally a (meth)acrylate monomer (C) without having an aryl group, or a cross-linking monomer (D), or both the monomers (C) and (D), wherein an amount of the macromonomer (A) is in a range from 11 to 30% relative to a total mass of the macromonomer (A), the (meth)acrylate monomer (B), the (meth)acrylate monomer (C) when present, and the cross-linking monomer (D) when present, in the liquid monomer mixture,

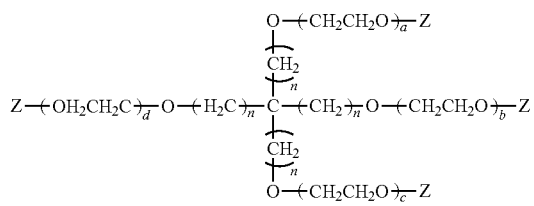

(I)

in the formula (I), four n's independently representing 1 or 2, a, b, c, and d independently being integers of 4 or more, and four Z's independently being substituent groups containing a (meth)acryloyl group, and wherein the (meth)acrylate monomer (B) is represented by following formula (II),

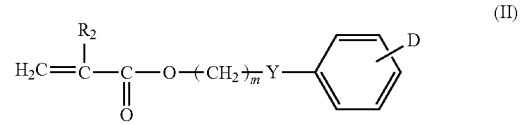

(II)

in the formula (II), $R_2$ is a hydrogen atom or a methyl group, m is an integer from 1 to 6, Y is a direct bond or an oxygen atom, and D is a hydrogen atom, $-C_6H_5$, $-CH_2C_6H_5$, or $-OC_6H_5$.

2. The polymer material of claim 1, wherein in the formula (I), the a, b, c, and d are independently integers from 4 to 14, and a total of the a, b, c, and d is an integer from 16 to 56.

3. The polymer material of claim 1, wherein in the formula (I), the four Z's are independently represented by formula (Z1), formula (Z2), or formula (Z3) below:

(Z1)

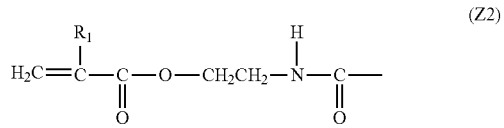

(Z2)

-continued

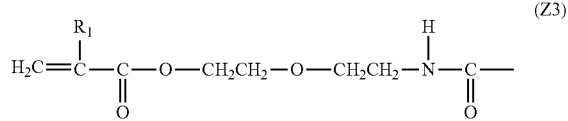

in each of the formula (Z1), the formula (Z2), and the formula (Z3), $R_1$ is a hydrogen atom or a methyl group.

4. The polymer material of claim 1, wherein in the formula (I), the four Z's are identical.

5. The polymer material of claim 4, wherein in the formula (I), each Z of the four Z's is an acryloyl group.

6. The polymer material of claim 1, wherein an amount of the (meth)acrylate monomer (B) is in a range from 70 to 89% relative to the total mass of the macromonomer (A), the (meth)acrylate monomer (B), the (meth)acrylate monomer (C) when present, and the cross-linking monomer (D) when present, in the liquid monomer mixture.

7. The polymer material of claim 1, wherein the liquid monomer mixture further comprises a polymerizable monomer with ultraviolet absorptivity.

8. The polymer material of claim 1, wherein the liquid monomer mixture further comprises a polymerizable monomer with a dyeing property.

9. The polymer material of claim 1, wherein the liquid monomer mixture comprises at least one monomer selected from the group consisting of the (meth)acrylate monomer (C) and the cross-linking monomer (D).

10. The polymer material of claim 1, wherein the polymer material is an intraocular lens material.

11. An intraocular lens, comprising a processed article of the intraocular lens material of claim 10.

12. An intraocular lens, comprising the polymer material of claim 1.

13. The polymer material of claim 1, wherein the liquid monomer mixture comprises the (meth)acrylate monomer (C).

14. The polymer material of claim 1, wherein the liquid monomer mixture comprises the cross-linking monomer (D).

* * * * *